(12) United States Patent
Myers et al.

(10) Patent No.: US 8,312,569 B2
(45) Date of Patent: Nov. 20, 2012

(54) WEARING APPAREL FOR USE BY ONE CONFINED TO A SITTING OR PRONE CONDITION

(76) Inventors: Shon Phillip Myers, Yucca Valley, CA (US); Danny Myers, Yucca Valley, CA (US)

( * ) Notice: Subject to any disclaimer, the term of this patent is extended or adjusted under 35 U.S.C. 154(b) by 120 days.

(21) Appl. No.: 12/806,036

(22) Filed: Aug. 5, 2010

(65) Prior Publication Data
US 2012/0030865 A1    Feb. 9, 2012

(51) Int. Cl.
*A41B 9/00* (2006.01)
(52) U.S. Cl. .......................................................... 2/400
(58) Field of Classification Search .................. 2/400, 2, 2/402–406; 450/98; 604/385.14, 385.01, 604/385.13
See application file for complete search history.

(56) References Cited

U.S. PATENT DOCUMENTS

| | | | |
|---|---|---|---|
| 1,695,109 A * | 12/1928 | Kosloff ........................ 604/396 |
| 2,807,805 A * | 10/1957 | Allan ............................... 2/404 |
| 4,382,443 A | 5/1983 | Shafer et al. | |
| 4,567,887 A | 2/1986 | Couch, Jr. | |
| 4,969,216 A * | 11/1990 | Guelli ............................. 2/400 |
| 5,103,501 A | 4/1992 | Melsels | |
| 5,749,101 A * | 5/1998 | Breindel ......................... 2/403 |
| 6,475,201 B2 | 11/2002 | Saito et al. | |
| 6,715,185 B2 | 4/2004 | Angellotti | |
| 7,504,955 B2 | 3/2009 | Overturf | |
| 7,727,218 B2 * | 6/2010 | Lavon et al. .................. 604/395 |
| 8,075,542 B2 * | 12/2011 | Lavon et al. ............. 604/385.14 |
| 2004/0046668 A1 | 3/2004 | Smith et al. | |

* cited by examiner

*Primary Examiner* — Danny Worrell
(74) *Attorney, Agent, or Firm* — Paul R. Martin

(57) ABSTRACT

A wearing apparel garment, such as an undergarment, has a padded portion positioned to be located adjacent to the coccyx of the wearer during use and which has a medicated patch containing suitable medicine therein which is applied to the user adjacent his or her coccyx during use. The garment is intended for use by one who is confined to a significant period of sitting or prone positioning which may make that person susceptible to pressure sores. The padded portion can be removed and the pad replaced as suitable. With the pad removed, the garment can be washed, if desired. The pad can be sized and medicated according to the need. The garment has no internal seams which might cause chafing or pressure on susceptible tissues. The garment is opened along a line which extends between the upper rim of the garment to the lower rim of the garment and which is releasably closed by a releasable fastener, such as a hook-and-loop fastener system.

4 Claims, 2 Drawing Sheets

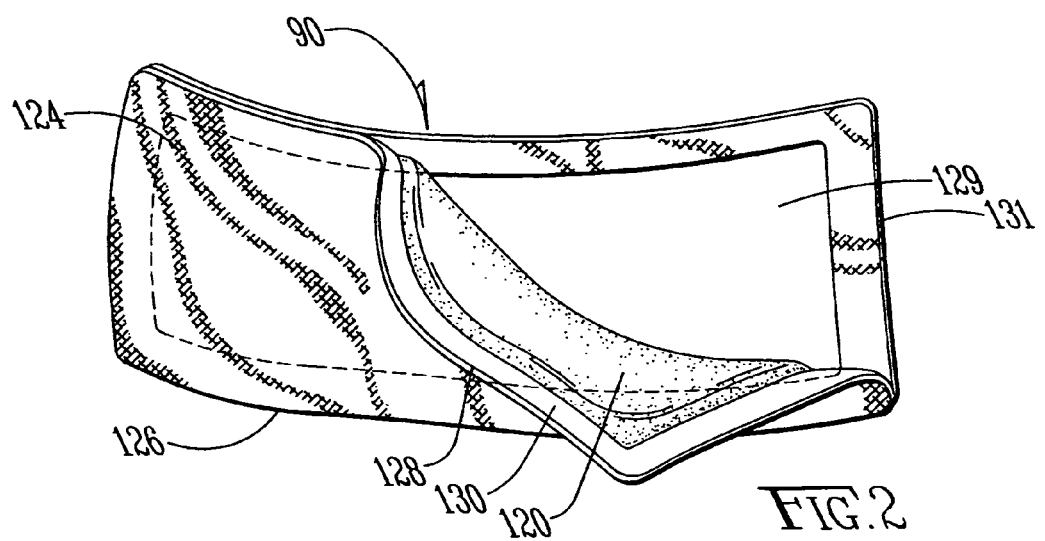

WEARING APPAREL FOR USE BY ONE CONFINED TO A SITTING OR PRONE CONDITION

TECHNICAL FIELD OF THE INVENTION

The present invention relates to the general art of wearing apparel, and to the particular field of garments worn by those confined to a wheelchair or to a bed for substantial lengths of time.

BACKGROUND OF THE INVENTION

People confined to a bed or wheelchair are susceptible to decubitus ulcers, commonly known as pressure or bedsores. Sitting or lying in bed for an excessive duration of time exerts a certain degree of pressure to an area of the person's skin. Pressure sores are at the very least annoying, and at worst dangerous and painful. Accordingly, those who must spend long periods of time in a sitting position must take care to either avoid such sores or to treat them in a prompt and effective manner. These ulcers are often seen to develop within soft tissue that is compressed between a bed or chair surface and a patient's weight-bearing bony prominences, the compressed tissue being at least partially deprived of oxygenated blood flow. A continued lack of blood flow, and resultant lack of oxygen, can result in cell death which may be evidenced in the form of pressure sores. Pressure sores do not become apparent immediately, but rather form over time, with the development speed depending on a number of factors including the firmness and friction of the supporting surface against the patient's skin, the patient/ambient temperature, the amount of moisture in contact with the skin, and the health and susceptibility of the skin due to age or illness. Thus, it is well known that individuals who are confined to wheelchairs or stationary chairs for extended periods of time are susceptible to the development of ischaemie or decubitus ulcers on their buttocks and thighs, particularly in areas where only small amounts of tissue separate bony structure from the surface of the skin These ulcers are caused by a lack of circulation of blood in the lower extremities, and by prolonged pressure on thin tissue areas.

Many months of treatment, and quite often surgery, are required to heal these ulcerations, to say nothing of the pain, the expense and the complete loss of productivity of the patient, with no assurance that the condition will not recur. This excessive pressure occludes the person's capillaries and cuts off the supply of blood to his or her tissue thus causing the aforementioned sores. Pressure sores can cause tissue necrosis and can damage muscle, bone and supporting structure, and as such can be a severe medical problem and life threatening. In some instances, pressure sores can be avoided by simply alleviating pressure on an individual's skin through movement or weight shifting.

People that have a normal range of motion and normal sensation will experience discomfort and adjust or shift their weight prior to the formation of pressure sores. Individuals confined to a wheelchair, paraplegics or quadriplegics for example, may be capable of shifting their weight but may not have adequate sensation to know when to perform such a weight shift.

Prior devices that have been developed in order to prevent the formation of pressure sores include cushion systems that are inflatable. Some of these cushion systems employ air bags that can be inflated to different pressures or inflated at different locations on the wheelchair. Cushion systems thus seek to alternate the pressure points upon the individual's body thus reducing the occurrence of pressure sores. Prior devices have also been proposed that measure the amount of movement of the individual within his or her wheelchair. If an insufficient amount of movement is detected, the system assumes that the individual is not shifting his or her weight enough within the wheelchair and an alarm goes off informing the individual that a weight shift must be performed. Additional devices have been proposed that measure the amount of pressure the individual exerts onto the seat for a given time. If the amount of pressure for a given time is attained, the device signals the individual that it is time to perform a weight shift.

Previous attempts to reduce the formation of pressure sores, while enjoying a degree of success, are either too costly or are not easy to utilize over extended periods of time. Additionally, these systems are often complicated and signal alerts based upon a variety of detection parameters thus increasing the chances that the system may fail to issue a required alarm. Previous systems are not conservative in that they are designed to signal an alarm based on analyzing multiple conditions, such as pressure and time, to determine if these conditions justify issuing an alert. Although weight shifting is a good way to prevent pressure sores, to be effective the practice must become a habit.

Therefore, there is a need for a means that effectively prevents and/or relieves pressure sores associated with long periods of sitting.

Common sites of such sores are the hips or buttocks, caused by restricted circulation as well as compression of tissue between ilia, ischia or coccyx bones, and seats or mattresses. Severe medical problems can result when one who is helpless and confined to wheelchair or bed is left unattended for extended periods.

Persons with such immobility, including those who have lost the use of and, often the sensation in, their lower body, particularly their legs, are especially prone to suffer from this problem. Although pads for wheelchairs are available and effective for many purposes, and are widely used, they are not easily transferred from wheelchair to automobile, sofa, chair or, more commonly, to floor, for use when sitting thereon. The floor is a favorite place for those who wish to be as active as possible, some of whom use it as a place of work, recreation or even relaxation.

It is estimated that more than two-thirds of pressure sores suffered by wheelchair-bound individuals occur during the time they are not in their wheelchairs. Partially, this is because it is difficult and awkward for such a person to move between the floor and a wheelchair, so they tend to stay in one place or the other. Also, however, it is inconvenient and sometimes ineffective to move a cushioning pad between wheelchair and floor, and to keep it in place when moving about on the floor.

Paraplegics and other persons who have lost the use of their lower body, particularly their legs, are especially prone to suffer from this problem because they must depend primarily upon wheelchairs and the like for locomotion, which are not always the most comfortable places to sit. Also, they cannot always sit on padded seats and, because they have no sensation in the affected areas, they are not aware of any discomfort which might otherwise be relieved by squirming about. It can be seen that prevention is especially important to such persons in such situations. Most paraplegics use their arms to propel themselves about from place to place on the floor, particularly if they have developed substantial upper-body strength, and especially if they live alone, where they have control over their environment.

These activities, combined with frequent slidings about, can cause pressure and abrasion sores and, sometimes, bruises or even lacerations from colliding with walls, corners, furniture, and other solid obstacles found everywhere in the average dwelling. These hazards are especially critical because of the lack of sensation in lower body parts which many persons have; even if they suffer an injury, they may be unaware of it until it has become infected. Minor collisions during normal daily activities, i.e., bumping into table legs, stubbing a toe, etc., can cause injuries which can deteriorate into serious medical problems if continually irritated by the same activities, and can have adverse health consequences. The skin of a person suffering from the kind of disabilities described herein can become so vulnerable to breakdown, that constant pressure or abrasion even by clothing seams can cause injury. Consequently, prevention becomes very important.

Therefore, more specifically, there is a need for a device to prevent or relieve bed sores associated with pressure over the coccyx and the bony prominence on the posterior aspect of the coccyx bone.

SUMMARY OF THE INVENTION

These, and other, objects are achieved by a wearing apparel garment, such as an undergarment, which is intended for use by a person who may be confided to a significant time in a sitting or prone position such that the person is susceptible to pressure sores. The garment has a padded portion positioned to be located adjacent to the coccyx of the wearer during use and which has a medicated patch containing suitable medicine therein which is applied to the user adjacent his or her coccyx during use. Further, the pad can be sized and medicated according to the need. The medication can include antibiotics, emoluments, lotions or the like as well and the like as needed or as suitable. The garment has no internal seams which might cause chafing or pressure on susceptible tissues. The garment is opened along a line which extends between the upper rim of the garment to the lower rim of the garment and which is releasably closed by a releasable fastener, such as a hook-and-loop fastener system. The need for adhesive fasteners is thus avoided as such fasteners, including adhesive tape, tend to lead to skin irritation.

The padded garment is intended for use by those persons who, because of a variety of circumstances, must spend a great deal of their time lying in bed, or sitting, particularly in a wheelchair. As is well known, such persons often develop "bed-sores", or "pressure-sores", because of the restricted blood circulation described hereinbefore.

Using the garment embodying the present invention provides many benefits. For example, the garment is easy and convenient to use and is easily disposable and inexpensive; no medical tape is required thereby reducing skin abrasions around the wound which, over time, may cause the skin to tear which will, at the least, slow the process of wound healing. The garment embodying the present invention includes medicated ¾" gauze which keeps the area around the wound in good health which, in turn, allows all attention to be directed to healing the pressure sore. Furthermore, since the medicated pad is securely held in place, the pressure sore is not undermined by having gauze pressed into the wound as a person slides or moves about. The patch on which the pad is mounted is easily removed for service or the like.

Other systems, methods, features, and advantages of the invention will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWING FIGURES

The invention can be better understood with reference to the following drawings and description. The components in the figures are not necessarily to scale, emphasis instead being placed upon illustrating the principles of the invention. Moreover, in the figures, like referenced numerals designate corresponding parts throughout the view.

FIG. 2 is a detailed view of the patch unit of the wearing apparel garment embodying the principles of the present invention.

DETAILED DESCRIPTION OF THE INVENTION

Figure 1:
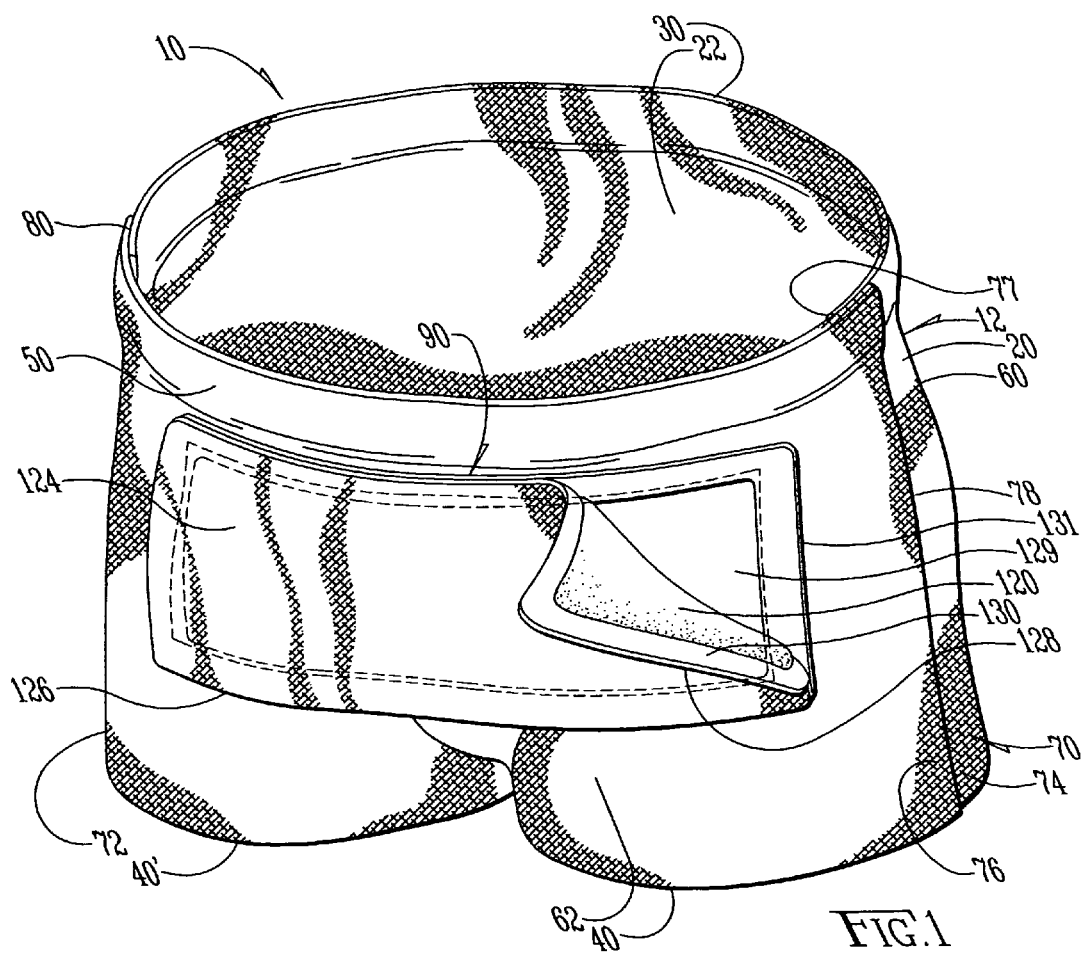
FIG. 1 is a rear perspective view of a wearing apparel garment embodying the principles of the present invention.

Referring to FIGS. 1 and 2, it can be understood that the present invention is embodied in an item of wearing apparel, such as an undergarment 10, that is intended to be worn by a person who will be in a sitting or prone position for a significant amount of time and thus be in danger of developing pressure sores, especially in their buttocks area. Garment 10 is intended to prevent or alleviate such sores.

As can be understood from FIG. 1, garment 10 includes a body portion 12 that is sized and adapted to be worn adjacent to the buttocks and hips area of a wearer in the manner of an undergarment, such as boxer shorts. Body portion 12 includes a first surface 20 which is an outer surface when the body portion is being worn, a second surface 22 which is an inner surface when the body portion is being worn. The inner surface will be located adjacent to the skin of the wearer. Body portion 12 further includes a first rim 30 which is a top rim when the body portion is being worn and a second rim 40 which is a bottom rim when the body portion is being worn. As can be understood from FIG. 1, there are two bottom rims, 40 and 40', which surround the legs of the wearer. A waist band 50 can be formed of elastic or the like and is located in the top rim to secure the body portion to the wearer.

Body portion 12 further includes a first area 60 that is a front portion when the body portion is worn and a second area 62 which is a rear portion, and will be located adjacent to the wearer's buttocks, when the body portion is worn. A first side area 70 extends from the top rim to bottom rim 40 and a second side area 72 extends from the top rim to bottom rim 40'. The side portions are identical and each of the side portions is divided into a first portion 74 on front portion and a second portion 76 on the rear portion with terminal ends 77 and 78 respectively that are positioned closely adjacent to each other to close the body portion about the wearer. Closure means 80, such as hook-and-loop fastening means, or the like, is used to releasably hold the terminal ends together after the garment has been donned by the wearer. The terminal ends can be opened up to allow the garment to be donned or removed. Allowing the garment to be opened using the closure means defined by the terminal ends and the releasable closure means allows the garment to be easily donned and removed. The garment itself is also disposable.

A patch unit 90 is mounted on the body portion. As seen in FIGS. 1 and 2, the rear portion 62 of the wearing apparel 10 has a three sided cutout section 124 that is hinged at the bottom 126, thus forming a flap 128 which has three free edges, i.e., at both sides and the top. The bottom 126 is connected to and contiguous with the rear portion 62 of the wearing apparel 10. When the flap 128 is open, it defines an open space 129 in the rear portion of the wearing apparel 10.

An adhesive strip 130 overlies and surrounds the three open edges of the flap 128, and extends beyond the edges thereof. The area surrounding the open space 129 in the rear portion 62 optionally has an adhesive material 131 applied thereto. When the flap 128 is closed, it is brought into relationship with the rear portion 62. The adhesive strip 120 surrounding the three sides of the flap 128 comes into contact with the adhesive material 131 surrounding the open space 129 in the rear portion 62, thus enabling the flap 128 to be secured to the rear portion 62. The adhesive strip 130 and adhesive material 131 are the same as commonly used in wound coverings such as adhesive bandages, sold by the Safeway Corporation, Pleasanton, Calif., or Johnson and Johnson Consumer companies, Inc., Skillman, N.J., under the trademarked name of Band-Aid.

A pad 120 is releasably mounted on the inside surface of the flap 128 of patch unit 90 to be located within the perimeter of the open space 129 when the patch unit 90 is in the covering relationship with the open space 129 as shown in the figures. Releasable fastening means, can be located on the patch unit 90 and on the pad element adjacent 120 to the perimeter of the pad element to releasably mount the pad element on the patch unit in position to contact the wearer's skin that is located adjacent to the cutout when the body portion is being worn. Medicine or emolument or lotion or the like can be located in the pad to contact the wearer's skin when the body portion is being worn. The pad 120 can be of variable thickness, preferably ranging from about 1½ to 2 inches in thickness. The pad 120 can also be manufactured in various sizes, and adapted to fit over pressure sores of varying dimensions.

In a preferred embodiment of the invention, the inside surface of the rear portion 62 of the garment 10 is constructed with an absorbent gauze surrounding the four edges of opening 129. Preferably, the gauze is about 2 inches wide, i.e, it extends about 2 inches from an edge of opening 129, and is about ¾ inch thick. The purpose of the gauze is to catch and absorb any drainage or liquid substances that may come from a wound or medicine used to pack in the wound if the wound is opened The undergarment of this invention can be adapted to fit all shapes and sizes from children to grown adults, from small to extra large.

The undergarment of this invention can be manufactured with a variety of medications, antibiotics or lotions available separate from, or in the pad 120, so a patient will be free to choose what medication he or she is comfortable with.

While various embodiments of the invention have been described, it will be apparent to those of ordinary skill in the art that many more embodiments and implementations are possible within the scope of this invention. Accordingly, the invention is not to be restricted except in light of the attached claims and their equivalents.

What is claimed is:

1. An undergarment for use by a person who is confined to a sitting or prone position for long periods of time comprising:
    a body portion that is sized and adapted to fit around the buttocks portion of a wearer when worn, the body portion having a first surface which is an outer surface when the body portion is being worn, a second surface which is an inner surface when the body portion is being worn and which is located adjacent to the skin of the wearer when the body portion is being worn, a first area that is a front portion when the body portion is being worn, a second area that is a rear portion and is located adjacent to the wearer's buttocks when the body portion is being worn, and first and second side areas which are located adjacent to the wearer's hips when the body portion is being worn;
    a closure member located on at least one side area of the body portion and which includes a first portion associated with the first area of the body portion, a second portion associated with the second area of the body portion, and a releasable fastener on the first and second areas adjacent to the first and second portions of the closure member which releasably attaches the first and second portions of the closure member together when the first and second portions of the closure member are engaged with each other; and
    a medicated patch portion on the second area of the body portion and positioned on the second area of the body portion to be located adjacent to the coccyx area of the wearer when the body portion is being worn, the medicated patch portion including
        (1) an opening defined through the body portion,
        (2) a patch element which has a first surface that is an outside surface when the patch element is in use and a second surface which is an inside surface when the patch element is in use, the patch element being in use when it is in position to have the inner surface thereof in contact with the skin of the wearer when the body portion is being worn,
        (3) releasable fastening means on the patch element and corresponding releasable fastening means on the outside surface of the body portion adjacent to the opening, the releasable fastening means on the patch element and on the body portion cooperating to releasably mount the patch element on the outer surface of the body portion in position to cover the opening when the fastening means on the patch element is engaged with the fastening means on the outside surface of the body portion, and
        (4) a medicated pad element releasably mounted on the inside surface of the patch element in position to contact the skin of the wearer when the body portion is being worn.

2. The undergarment defined in claim 1 wherein the body portion includes a first rim which is a top rim when the body portion is being worn and a second rim which is a bottom rim when the body portion is being worn, the closure member extending from adjacent to the top rim to adjacent to the bottom rim.

3. The undergarment defined in claim 2 further including a second closure member located on another side area of the body portion.

4. A wearing apparel garment for use by a person who is confined to a sitting or prone position for long periods of time comprising:
    a body portion that is sized and adapted to fit around the buttocks portion of a wearer when worn, the body portion having a first surface which is an outer surface when the body portion is being worn, a second surface which is an inner surface when the body portion is being worn and which is located adjacent to the skin of the wearer when the body portion is being worn, a first area that is a front portion when the body portion is being worn, a second area that is a rear portion and is located adjacent to the wearer's buttocks when the body portion is being worn, and first and second side areas which are located adjacent to the wearer's hips when the body portion is being worn;

a closure member located on at least one side area of the body portion and which includes a first portion associated with the first area of the body portion, a second portion associated with the second area of the body portion, and a releasable fastener on the first and second areas adjacent to the first and second portions of the closure member which releasably attaches the first and second portions of the closure member together when the first and second portions of the closure member are engaged with each other; and a medicated patch portion on the second area of the body portion and positioned on the second area of the body portion to be located adjacent to the coccyx area of the wearer when the body portion is being worn, the medicated patch portion including
  (1) an opening defined through the body portion,
  (2) a patch element which has a first surface that is an outside surface when the patch element is in use and a second surface which is an inside surface when the patch element is in use, the patch element being in use when it is in position to have the inner surface thereof in contact with the skin of the wearer when the body portion is being worn,
  (3) releasable fastening means on the patch element and corresponding releasable fastening means on the outside surface of the body portion adjacent to the opening, the releasable fastening means on the patch element and on the body portion cooperating to releasably mount the patch element on the outer surface of the body portion in position to cover the opening when the fastening means on the patch element is engaged with the fastening means on the outside surface of the body portion, and
  (4) a medicated pad releasably mounted on the inside surface of the patch element in position to contact the skin of the wearer when the body portion is being worn.

\* \* \* \* \*